(12) United States Patent
Takizawa et al.

(10) Patent No.: US 7,863,696 B2
(45) Date of Patent: Jan. 4, 2011

(54) SEMICONDUCTOR SENSOR AND METHOD FOR MANUFACTURING THE SAME

(75) Inventors: Teruo Takizawa, Matsumoto (JP); Takayuki Kondo, Chino (JP); Masayoshi Todorokihara, Shimosuwa (JP)

(73) Assignee: Seiko Epson Corporation (JP)

( * ) Notice: Subject to any disclaimer, the term of this patent is extended or adjusted under 35 U.S.C. 154(b) by 213 days.

(21) Appl. No.: 12/336,846

(22) Filed: Dec. 17, 2008

(65) Prior Publication Data

US 2009/0184381 A1 Jul. 23, 2009

(30) Foreign Application Priority Data

Jan. 23, 2008 (JP) .............................. 2008-012925

(51) Int. Cl.
*H01L 27/14* (2006.01)
*H01L 21/00* (2006.01)

(52) U.S. Cl. ........................................ 257/414; 438/49
(58) Field of Classification Search ................. 257/414; 438/49; 310/313 R; 29/25.35
See application file for complete search history.

(56) References Cited

U.S. PATENT DOCUMENTS 5,296,125 A * 3/1994 Glass et al. .................. 430/311
2009/0267164 A1* 10/2009 Wunnicke et al. ........... 257/414

FOREIGN PATENT DOCUMENTS

| JP | 2006-220546 | 8/2006 |
|---|---|---|
| JP | 2007-093573 | 4/2007 |
| JP | 2007-147556 | 6/2007 |

OTHER PUBLICATIONS

"CMOS Integrated Gas Sensor Chip Using SAW Technology"; Sharokh Ahmadi, Can Korman, Mona Zaghloul, and Kuan-Hsun Huang; Department of Electrical and Computer Engineering, The George Washington University, Washington DC 20052; Circuits and Systems, 2003, ISCAS '03, Proceedings of the 2003 International Symposium on Circuits and Systems, Published May 25-28, 2003.

(Continued)

*Primary Examiner*—Lex Malsawma
(74) *Attorney, Agent, or Firm*—Harness, Dickey & Pierce, P.L.C.

(57) ABSTRACT

A semiconductor sensor includes: a semiconductor substrate; a plurality of piezoelectric thin films layered on the semiconductor substrate, the plurality of piezoelectric thin films including at least a pair of the piezoelectric thin films layered above and below; a pair of electrodes that are formed at an interface of at least the pair of the piezoelectric thin films layered above and below and excite surface acoustic waves; a thin film directly under a lowest-layer piezoelectric film of the piezoelectric thin films; a metal thin film that is formed at an interface of the lowest-layer piezoelectric thin film and the thin film, and facilitate a growth of a ridge-and-valley portion on a surface of an uppermost-layer piezoelectric thin film of the piezoelectric thin films; and a sensitive film for molecular adsorption formed on at least the ridge-and-valley portion on the uppermost-layer piezoelectric thin film.

14 Claims, 9 Drawing Sheets

OTHER PUBLICATIONS

"CMOS-based chemical microsensors"; Andreas Hierlemann and Henry Baltes; Physical Electronics Laboratory, ETH Zurich, Honggerberg, HPT H 4.2, CH-8093 Zurich, Switzerland; Analyst, 2003, 128, 15-28.

"Synthesis of C-Axis-Oriented AlN Thin Films on High-Conducting Layers: Al, Mo, Ti, TiN, and Ni"; Gonzalo F. Iriarte, Johan Bjurstrom, Jorgen Westlinder, Fredrik Engelmark, and Ilia V. Katardjiev; IEEE Transactions on Ultrasonics, Ferroelectrics, and Frequency Control, vol. 52, No. 7, Jul. 2005.

* cited by examiner

SEMICONDUCTOR SENSOR AND METHOD FOR MANUFACTURING THE SAME

BACKGROUND

1. Technical Field

The present invention relates to a semiconductor sensor and a method for manufacturing the semiconductor sensor.

2. Related Art

Recently, chemical sensors, odor sensors, gas sensors, and the like that detect chemical substances in the air have been developed in response to increasing awareness of environmental issues. In the sensors, a sensitive film on which chemical substances adsorb is formed on a piezoelectric element, such as a quartz crystal resonator and a surface acoustic wave element, and the mass change of the sensitive film corresponds to the oscillation frequency change of the piezoelectric element. As a result, the chemical substances can be detected by using the mass change.

For example, JP-A-2007-147556 discloses a method for manufacturing a thin film (sensitive film) and a chemical sensor using the thin film manufactured by the method. In order to improve adsorption sensitivity (i.e., the sensitivity of the sensor), the method includes: a step for mixing a sensitive film material and fine particles; a step for forming a thin film with a mixture of the sensitive film material and the fine particles; a step for drying the thin film; and a step for removing the fine particles exposed at the thin film surface after being dried, thereby increasing the adsorption area of the thin film.

The related art described above has a problem in that such particular steps are additionally required in order to improve the adsorption sensitivity of the sensitive film, increasing the manufacturing costs and the price of the chemical sensor.

SUMMARY

An advantage of the invention is to provide a semiconductor sensor having a high sensitivity with a low price, and a method for manufacturing the semiconductor sensor.

According to a first aspect of the invention, a semiconductor sensor includes: a semiconductor substrate; a plurality of piezoelectric thin films layered on the semiconductor substrate, the plurality of piezoelectric thin films including at least a pair of the piezoelectric thin films layered above and below; a pair of electrodes that are formed at an interface of at least the pair of the piezoelectric thin films and excite surface acoustic waves; a thin film directly under a lowest-layer piezoelectric film of the piezoelectric thin films; a metal thin film that is formed at an interface of the lowest-layer piezoelectric thin film and the thin film, and facilitate a growth of a ridge-and-valley portion on a surface of an uppermost-layer piezoelectric thin film of the piezoelectric thin films; and a sensitive film for molecular adsorption formed on at least the ridge-and-valley portion on the uppermost-layer piezoelectric thin film.

In the semiconductor sensor, the metal thin film formed at the interface of the lowest-layer piezoelectric thin film and the thin film directly under the lowest-layer piezoelectric thin film can produce the ridge-and-valley portion on the surface of the uppermost-layer piezoelectric thin film. That is, the surface area of the sensitive film for molecular adsorption formed on the surface of the uppermost-layer piezoelectric thin film (i.e., molecular adsorption area) can be enlarged, providing a semiconductor sensor having a high sensitivity. In addition, the metal thin film can be formed by using conventional semiconductor manufacturing processes without employing a particular process for enlarging the surface area of the sensitive film as necessary in related art, e.g., JP-A-2007-147556. Thus, the manufacturing costs can be reduced. Consequently, a semiconductor sensor having a high sensitivity can be provided with low price.

In the sensor, the metal thin film is preferably a metal facilitating a crystal growth of a wurtzite structure of the piezoelectric thin films in a c-axis direction.

The metal can facilitate the growth of the ridge-and-valley portion on the surface of the uppermost-layer piezoelectric thin film.

In addition, it is preferable that any one of Pt, Au, Al, Ag, Cu, Mo, Cr, Nb, W, Ni, Fe, Ti, Co, Zn, and Zr be used for the metal thin film.

The sensor preferably includes an oscillation circuit. The circuit preferably includes: an inverter circuit layered between the lowest-layer piezoelectric thin film and the semiconductor substrate; and a surface acoustic wave element having the metal thin film, the pair of the piezoelectric thin films, the pair of the electrodes, and the sensitive film. In the sensor, the inverter circuit and the acoustic wave element are preferably electrically coupled.

The oscillation frequency of such inverter type oscillation circuit depends on the frequency characteristics of the surface acoustic wave element. The frequency characteristics of the surface acoustic wave element vary depending on molecular adsorption amount of the sensitive film since the sensitive film on which molecules adsorb is provided to the surface acoustic wave element. Accordingly, the oscillation frequency of the oscillation circuit varies. Measuring the oscillation frequency change corresponding to the molecular adsorption amount with the frequency counter and the like outside the sensor allows detecting chemical substances in the air with a high sensitivity.

In the sensor, it is preferable that the inverter circuit include a CMOS circuit.

The inverter circuit including the CMOS circuit can provide a semiconductor sensor having a low power consumption and high response speed.

In the sensor, it is preferable that the oscillation circuit include a plurality of the oscillation circuits. The surface acoustic wave element included in at least one of the plurality of oscillation circuits is preferably used as a reference element having no sensitive film.

The oscillation frequency of the oscillation circuit including the surface acoustic wave element having no sensitive film, i.e., the reference element, is used as a reference frequency. Comparing the oscillation frequencies of the other oscillation circuits with the reference frequency allows more easily detecting the frequency varied by adsorption of gas molecules. As a result, a semiconductor sensor having a higher sensitivity can be provided.

According to a second aspect of the invention, a method for manufacturing a semiconductor sensor includes: (a) layering a plurality of piezoelectric thin films on a semiconductor substrate, the plurality of piezoelectric thin films including at least a pair of the piezoelectric thin films layered above and below; (b) forming a pair of electrodes at an interface of the pair of the piezoelectric thin films, the electrodes exciting surface acoustic waves; (c) forming a metal thin film at an interface of a lowest-layer piezoelectric thin film of the piezoelectric thin films and a thin film directly under the lowest-layer piezoelectric film, the metal thin film facilitating a growth of a ridge-and-valley portion on a surface of an uppermost-layer piezoelectric thin film of the piezoelectric thin films; and (d) forming a sensitive film for molecular adsorption at least on the ridge-and-valley portion on the uppermost-layer piezoelectric thin film.

According to the method, the surface area of the sensitive film for molecular adsorption formed on the surface of the uppermost-layer piezoelectric thin film (i.e., molecular adsorption area) can be enlarged, thereby allowing manufacturing a semiconductor sensor having a high sensitivity. In addition, the metal thin film can be formed by using conventional semiconductor manufacturing processes without employing a particular process for enlarging the surface area of the sensitive film as necessary in related art, e.g., JP-A-2007-147556. Thus, the manufacturing costs can be reduced. Consequently, a semiconductor sensor having a high sensitivity can be manufactured with low costs.

In the method, the metal thin film is preferably a metal facilitating a crystal growth of a wurtzite structure of the piezoelectric thin films in a c-axis direction.

In addition, it is preferable that any one of Pt, Au, Al, Ag, Cu, Mo, Cr, Nb, W, Ni, Fe, Ti, Co, Zn, and Zr be used for the metal thin film. Further, in step (c), it is preferable that the metal thin film be formed by using Pt with a thickness of 1000 angstrom or more.

The metal thin film formed with Pt with a thickness of 1000 angstrom or more can achieve the full-width at half-maximum of the X-ray diffraction pattern, which is an index of the crystal property, of 2 degrees or less.

In the method, it is preferable in step (a) that the lowest-layer piezoelectric thin film be formed with AlN by using a reactive sputtering method by sputtering a pure Al target in an atmosphere containing Ar and $N_2$ with a thickness of 8000 angstrom to 15000 angstrom under a film forming condition in which film forming pressure is within a range from 0.05 Pa to 2.0 Pa, a semiconductor substrate temperature is within a range of 150 degree centigrade to 400 degrees centigrade, and a flow rate ratio of Ar to $N_2$ is within a range of 0.0 to 1.0. The flow rate ratio of Ar to $N_2$ is 1.0 means that the gas flow rates are expressed as Ar : $N_2$=1:1.

With this film forming condition, the lowest-layer piezoelectric thin film, which is formed on the metal thin film, can grow as a columnar crystal orientated and aligned in the c-axis direction of the wurtzite structure so as to produce the ridge-and-valley portion corresponding to the grown crystal grain size on the uppermost surface of the lowest-layer piezoelectric thin film. In addition, since the piezoelectric thin film formed on the lowest-layer piezoelectric thin film grows following the surface morphology of the lowest-layer piezoelectric thin film, the crystal grain size grows larger, thereby allowing more enlarging the ridge-and-valley portion produced on the surface of the uppermost-layer piezoelectric thin film, i.e., more enlarging the surface area of the sensitive film.

The method preferably further includes: (e) forming an inverter circuit between the lowest-layer piezoelectric thin film and the semiconductor substrate; and (f) forming a wiring line electrically coupling a surface acoustic wave element including the metal thin film, the pair of the piezoelectric thin films, the pair of the electrodes, and the sensitive film, and the inverter circuit so as to structure an oscillation circuit.

The oscillation frequency of such inverter type oscillation circuit depends on the frequency characteristics of the surface acoustic wave element. The frequency characteristics of the surface acoustic wave element vary depending on molecular adsorption amount of the sensitive film since the sensitive film on which molecules adsorb is provided to the surface acoustic wave element. Accordingly, the oscillation frequency of the oscillation circuit varies. Measuring the oscillation frequency change corresponding to the molecular adsorption amount with the frequency counter and the like outside the sensor allows detecting chemical substances in the air with a high sensitivity.

In the method, it is preferable in step (e) that a CMOS circuit be formed as the inverter circuit.

The inverter circuit including the CMOS circuit can manufacture a semiconductor sensor having a low power consumption and high response speed.

In the method, it is preferable that the oscillation circuit include a plurality of the oscillation circuits. In this case, in step (d), it is preferable that the sensitive film be not formed in the surface acoustic wave element included in at least one of the plurality of oscillation circuits.

The oscillation frequency of the oscillation circuit including the surface acoustic wave element having no sensitive film, i.e., the reference element, is used as a reference frequency. Comparing the oscillation frequencies of the other oscillation circuits with the reference frequency allows more easily detecting the frequency varied by adsorption of gas molecules. As a result, a semiconductor sensor having a higher sensitivity can be manufactured.

BRIEF DESCRIPTION OF THE DRAWINGS

The invention will be described with reference to the accompanying drawings, wherein like numbers reference like elements.

DESCRIPTION OF EXEMPLARY EMBODIMENTS

Embodiments of the invention are described with reference to the accompanying drawings.

First Embodiment

Semiconductor Sensor

Figure 1A:
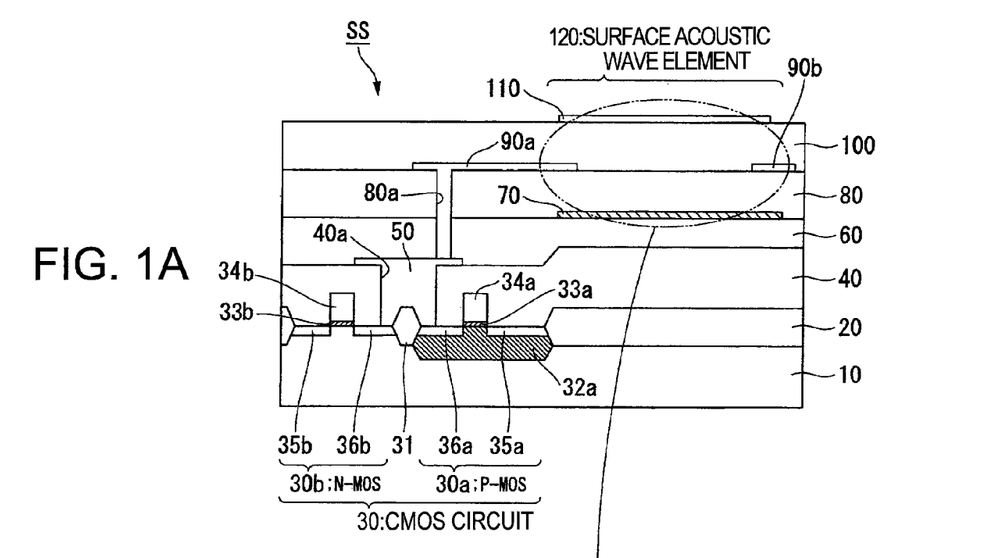
FIG. 1A is a sectional view of a semiconductor sensor according to an embodiment of the invention.
Figure 1B:
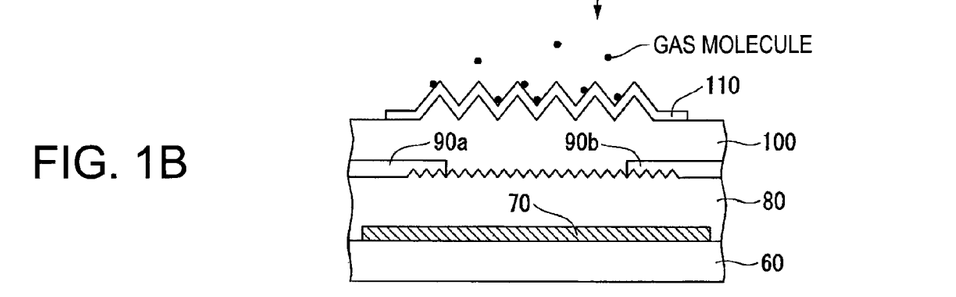
FIG. 1B is a detailed view of a portion of the semiconductor sensor of the embodiment.
Figure 2A:
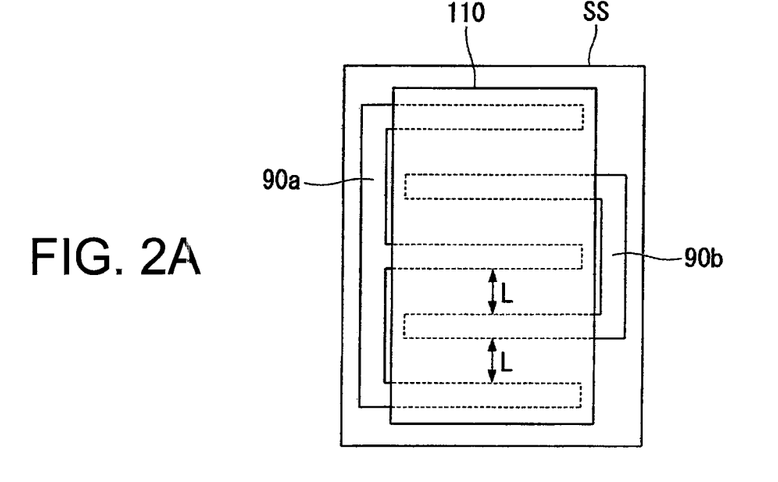
FIG. 2A is a top view of the semiconductor sensor of the embodiment.
Figure 2B:
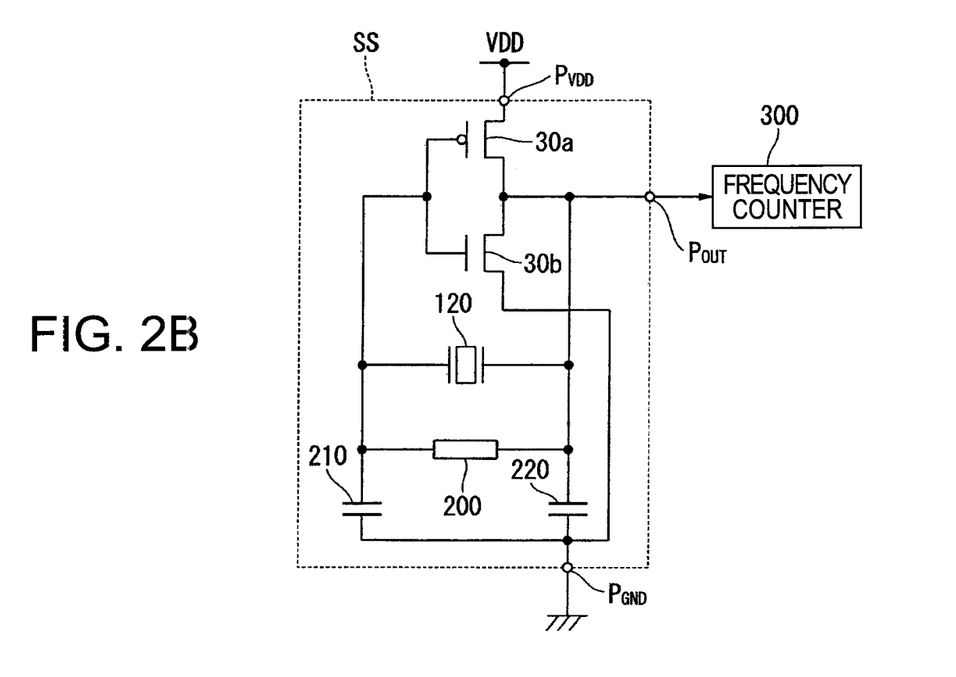
FIG. 2B is an equivalent circuit diagram of the semiconductor sensor of the embodiment.

FIG. 1A is a sectional view illustrating a semiconductor sensor SS according to a first embodiment of the invention. FIG. 1B is a detailed view of a portion of the semiconductor sensor SS shown in FIG. 1A. FIG. 2A is a top view of the semiconductor sensor SS. FIG. 2B is an equivalent circuit diagram of the semiconductor sensor SS.

As shown in FIG. 1A, the semiconductor sensor SS of the first embodiment includes a semiconductor substrate 10, a local oxidization of silicon (LOCOS) film 20, a complementary metal oxide semiconductor (CMOS) circuit 30, a first interlayer film 40, a CMOS output electrode 50, a second interlayer film 60, a metal thin film 70, a first piezoelectric thin film 80, a first electrode 90a, a second electrode 90b, a second piezoelectric thin film 100, and a sensitive film 110. The metal thin film 70, the first piezoelectric thin film 80, the first electrode 90a, the second electrode 90b, the second piezoelectric thin film 100 and the sensitive film 110 are included in a surface acoustic wave element 120.

The semiconductor substrate 10 is a silicon (Si) substrate. In the embodiment, a P-type Si substrate is exemplarily used. The LOCOS film 20 is a silicon oxide film formed on the semiconductor substrate 10 by a LOCOS separation method to electrically separate a CMOS circuit forming region and a surface acoustic wave element forming region.

The CMOS circuit 30 includes a separation insulation layer 31, a P channel type MOS transistor (hereinafter, referred to as a P-MOS transistor) 30a and an N channel type MOS transistor (hereinafter, referred to as an N-MOS transistor) 30b. The P-MOS transistor 30a and the N-MOS transistor 30b are electrically separated by the separation insulation layer 31. The P-MOS transistor 30a includes an N-type well 32a, a gate insulation film 33a formed on the N-type well 32a, a gate electrode 34a formed on the gate insulation film 33a, a source region 35a, and a drain region 36a. The N-type well 32a is formed by doping N-type impurity ions into the semiconductor substrate 10. The source region 35a and the drain region 36a are formed by doping P-type impurity ions into the N-type well 32a. The N-MOS transistor 30b includes a gate insulation film 33b formed on the semiconductor substrate 10, a gate electrode 34b formed on the gate insulation film 33b, a source region 35b, and a drain region 36b. The source region 35b and the drain region 36b are formed by doping N-type impurity ions into the semiconductor substrate 10.

The first interlayer film 40 is an insulation film formed on the LOCOS film 20 and the CMOS circuit 30 by a chemical vapor deposition (CVD) method or a spin coating method. Examples of the insulation film include a silicon dioxide ($SiO_2$) film, a tetra-ethoxy-silane (TEOS) film, a phosphor silicate glass (PSG) film, a boron phosphor silicate glass (BPSG) film, and combinations of them. In the embodiment, the first interlayer film 40 is composed of a $SiO_2$ film and a TEOS film deposited on the $SiO_2$ film. The first interlayer film 40 has a contact hole 40a coupling the CMOS circuit 30 and the surface acoustic wave element 120. The CMOS output electrode 50 serves as an output side electrode of the CMOS circuit 30 and formed by patterning, with a photolithography method, a metal layer (e.g. Al—Cu) deposited by a sputtering method on the contact hole 40a and the first interlayer film 40. That is, the CMOS output electrode 50 electrically connects the drain region 36a of the P-MOS transistor 30a and the drain region 36b of the N-MOS transistor 30b in the CMOS circuit 30. The second interlayer film 60 is an insulation film formed on the first interlayer film 40 by a CVD method. The same material used for the first interlayer film 40 can be used for the second interlayer film 60. In the embodiment, a TEOS film is used as the second interlayer film 60.

The metal thin film 70 is made of a metal having a function to facilitate a crystal growth of a wurtzite structure of the first piezoelectric thin film 80 in a c-axis direction, which will be described later. The metal thin film 70 is formed in the surface acoustic wave element forming region on the second interlayer film 60 by being patterned with a photolithography method. Examples of the metal used for the metal thin film 70 include platinum (Pt), gold (Au), aluminum (Al), silver (Ag), copper (Cu), molybdenum (Mo), chromium (Cr), niobium (Nb), tungsten (W), nickel (Ni), iron (Fe), titanium (Ti), cobalt (Co), zinc (Zn), zirconium (Zr), and combinations of them. In the embodiment, a combination of Ti and Pt is used.

The first piezoelectric thin film 80 is made of aluminum nitride (AlN) having piezoelectricity, and is formed by a reactive sputtering method on the second interlayer film 60 and the metal thin film 70. The piezoelectric material used for the piezoelectric thin film 80 may include metal oxide type piezoelectric materials such as zinc oxide (ZnO), lead zirconium titanate (PZT), lithium niobate ($LiNO_3$), and lithium tantalite ($LiTaO_3$). The first piezoelectric thin film 80 and the second interlayer film 60 have a via hole 80a electrically coupling the CMOS output electrode 50 and the first electrode 90a, i.e., wiring the CMOS circuit 30 and the surface acoustic wave element 120.

The first electrode 90a and the second electrode 90b are a pair of electrodes for exciting surface acoustic waves and formed by patterning, with a photolithography method, a metal layer (e.g., Al) deposited on the via hole 80a and the first piezoelectric thin film 80 by a sputtering method. As shown in FIG. 2A, the first electrode 90a and the second electrode 90b constitute an interdigital transducer having a distance L between the electrodes as a constant pitch. The first electrode 90a is electrically coupled to the CMOS output electrode 50 while the second electrode 90b is electrically coupled to an input electrode of the CMOS circuit 30. The input electrode of the CMOS circuit 30 is electrically coupled to the gate electrode 34a of the P-MOS transistor 30a and the gate electrode 34b of the N-MOS transistor 30b. In FIG. 1A, it is not shown.

The second piezoelectric thin film 100 is made of AlN having piezoelectricity as used for the first piezoelectric thin film 80, and formed by a reactive sputtering method on the first piezoelectric thin film 80, the first electrode 90a, and the second electrode 90b. The sensitive film 110 is a thin film on which molecules of chemical substances in the air adsorb, and formed in the surface acoustic wave element forming region on the second piezoelectric thin film 100 by being patterned with a photolithography method. Examples of the sensitive film 110 include a synthetic polymer film mainly containing polyester, polyamide, or the like, a natural polymer film such as lipid, and a silica series inorganic compound such as a silicone series polymer film.

The surface acoustic wave element 120 includes the metal thin film 70, the first piezoelectric thin film 80, the first electrode 90a, the second electrode 90b, the second piezoelectric thin film 100, and the sensitive film 110. Here, the metal thin film 70 has a function to facilitate the crystal growth of a wurtzite structure of the first piezoelectric thin film 80 in the c-axis direction. Thus, the first piezoelectric thin film 80, which is formed on the metal thin film 70, grows as a columnar crystal orientated and aligned in the c-axis direction of the wurtzite structure when the first piezoelectric thin film 80 is formed under predetermined film forming conditions. As a result, a ridge-and-valley portion corresponding to the grown crystal grain size is formed on the uppermost surface of the first piezoelectric thin film 80. In addition, the second piezoelectric thin film 100 grows following the surface morphology of the first piezoelectric thin film 80. Thus, the second piezoelectric thin film 100 grows to have a crystal grain size larger than that of the first piezoelectric thin film 80. As a result, the ridge-and-valley portion larger than that of the first piezoelectric thin film 80 is formed on the uppermost surface of the second piezoelectric thin film 100.

Since the sensitive film 110 is formed on the second piezoelectric thin film 100 on which the ridge-and-valley portion is formed, the sensitive film 110 has a similar ridge-and-valley portion. Thus, the surface area of the sensitive film 110 enlarges. That is, an area on which gas molecules adsorb can be enlarged, providing the semiconductor sensor SS having a high sensitivity. In addition, the metal thin film 70 can be formed by using conventional semiconductor manufacturing processes without employing a particular process for enlarging the surface area of the sensitive film 110 as necessary in related art, e.g., JP-A-2007-147556. Thus, the manufacturing costs can be reduced. Consequently, the semiconductor sensor SS having a high sensitivity can be provided with low price. A method for manufacturing the semiconductor sensor SS will be described in detail later.

The operation principle of the semiconductor sensor SS is described with reference to the equivalent circuit diagram shown in FIG. 2B. As shown in FIG. 2B, the semiconductor sensor SS includes the P-MOS transistor 30a and the N-MOS transistor 30b that are included in the CMOS circuit 30, the surface acoustic wave element 120, a feedback resistor 200, an input side capacitor 210 and an output side capacitor 220. The feedback resistor 200, the input side capacitor 210 and the output side capacitor 220 are not shown in FIG. 1A.

The output terminal of the CMOS circuit 30, i.e., the CMOS output electrode 50, is connected to one electrode of the surface acoustic wave element 120, i.e., the first electrode 90a, one terminal of the feedback resistor 200, and one terminal of the output side capacitor 220, and also connected to a frequency counter 300 provided outside the semiconductor sensor SS through an output terminal $P_{OUT}$. The input terminal of the CMOS circuit 30, i.e., the gate electrode 34a of the P-MOS transistor 30a and the gate electrode 34b of the N-MOS transistor 30b, is connected to the other electrode of the surface acoustic wave element 120, i.e., the second electrode 90b, the other terminal of the feedback resistor 200, and one terminal of the input side capacitor 210. A source electrode (not shown in FIG. 1A) of the P-MOS transistor 30a is connected to an external power source VDD through a power source terminal $P_{VDD}$. A source electrode (not shown in FIG. 1A) of the N-MOS transistor 30b is connected to the ground through a ground terminal $P_{GND}$. The other terminals of the input side capacitor 210 and the output side capacitor 220 are connected to the ground through the ground terminal $P_{GND}$.

That is, the semiconductor sensor SS includes an inverter type oscillation circuit in which the CMOS circuit 30 is used as an inverter and the surface acoustic wave element 120 is used as an oscillation element. The oscillation frequency of such inverter type oscillation circuit depends on the frequency characteristics of the surface acoustic wave element 120. The frequency characteristics of the surface acoustic wave element 120 vary depending on molecular adsorption amount of the sensitive film 110 since the sensitive film 110 on which molecules adsorb is provided to the surface acoustic wave element 120. As a result, the oscillation frequency of the oscillation circuit varies. Measuring the oscillation frequency change corresponding to the molecular adsorption amount with the frequency counter 300 outside the sensor allows chemical substances in the air to be detected with a high sensitivity. Here, the distance L between the first electrode 90a and the second electrode 90b that are included in the interdigital transducer is adequately set taking consideration into the wavelength of the oscillation frequency.

Second Embodiment

Method for Manufacturing a Semiconductor Sensor

A method for manufacturing the semiconductor sensor SS according to a second embodiment of the invention is described with reference to FIGS. 3A to 8B.

Figure 3A:
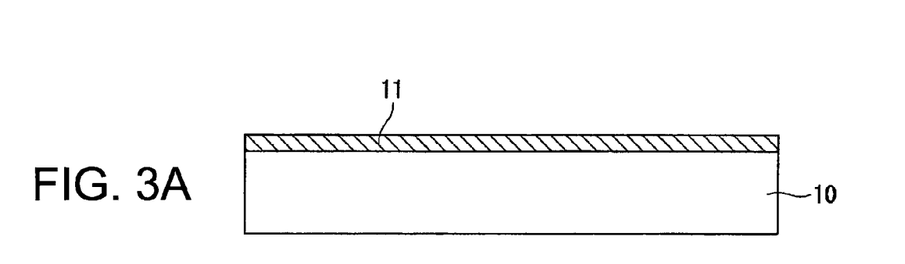
FIGS. 3A to 3D are explanatory views of a method for manufacturing the semiconductor sensor of the embodiment.
Figure 3B:
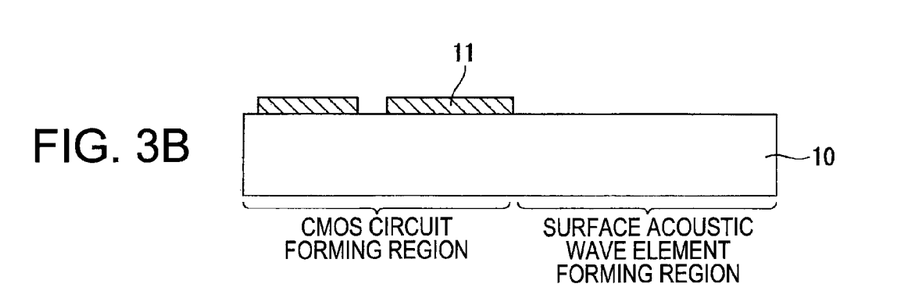
Figure 3C:
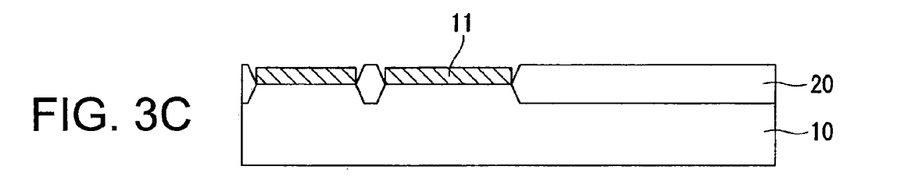
Figure 3D:
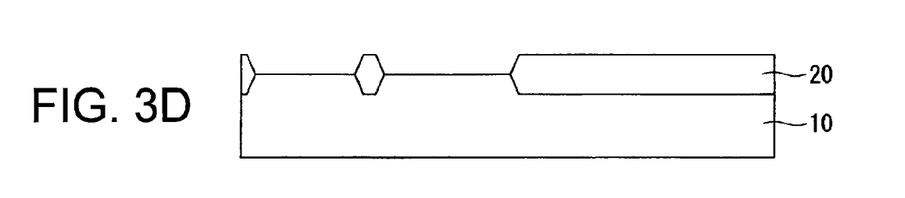

First, the CMOS circuit forming region and the surface acoustic wave element forming region are electrically separated on the semiconductor substrate 10 by using a LOCOS separation method. As shown in FIG. 3A, a silicon nitride film (SiNx) 11 is deposited on the semiconductor substrate 10 (P-type Si substrate) by using a CVD method. Then, as shown in FIG. 3B, the silicon nitride film 11 in the CMOS circuit forming region is left while the silicon nitride film 11 in the surface acoustic wave element forming region is removed (etched) by patterning the silicon nitride film 11 with a photolithography method. Next, as shown in FIG. 3C, a silicon oxide film (the LOCOS film 20) is formed by oxidizing, at a high temperature, a region from which the silicon nitride film 11 has been removed. Then, as shown in FIG. 3D, the silicon nitride film 11 left in the CMOS circuit forming region is removed with heated phosphoric acid after the LOCOS film 20 is formed.

Through the above steps, the CMOS circuit forming region and the surface acoustic wave element forming region are electrically separated on the semiconductor substrate 10.

Figure 4A:
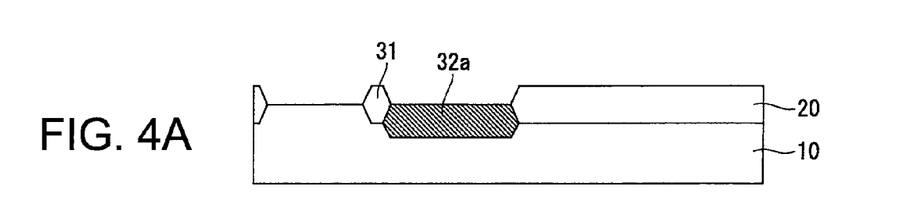
FIGS. 4A to 4D are explanatory views of the method for manufacturing the semiconductor sensor of the embodiment.
Figure 4B:
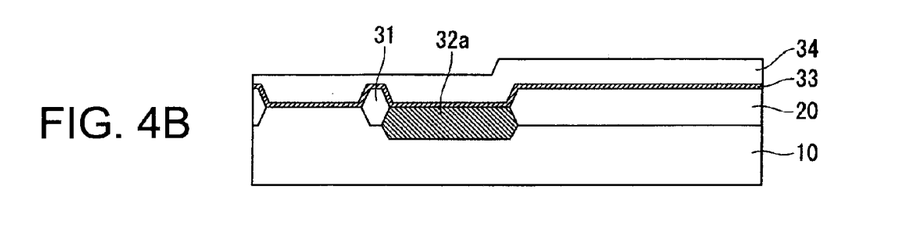

Subsequently, as shown in FIG. 4A, the separation insulation layer 31 is formed to electrically separate the P-MOS transistor 30a and the N-MOS transistor 30b in the CMOS circuit forming region on the semiconductor substrate 10, and then N-type impurity ions are doped into the semiconductor substrate 10 by an ion implantation method so as to from the N-type well 32a. The separation insulation layer 31 may be formed at the same time in forming the LOCOS film 20, or may be formed by using a shallow trench isolation (STI) method in a different step from one for forming the LOCOS film 20. Alternatively, the N-type impurity ions may be doped before the LOCOS film 20 is formed. Next, as shown in FIG. 4B, the gate insulation film 33 is formed on the semiconductor substrate 10 and the LOCOS film 20 by being thermally oxidized by using a CVD method, and then a poly-Si layer 34 serving as the gate electrode of the CMOS circuit 30 is deposited on the gate insulation film 33 by using a CVD method.

Figure 4C:
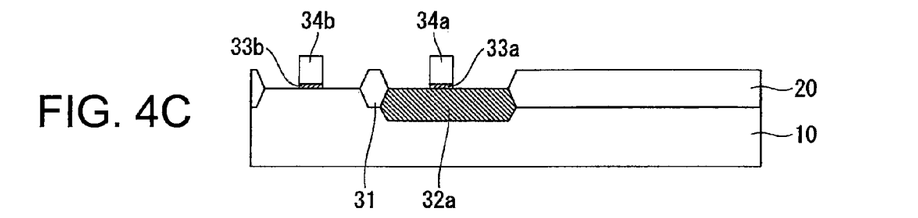
Figure 4D:
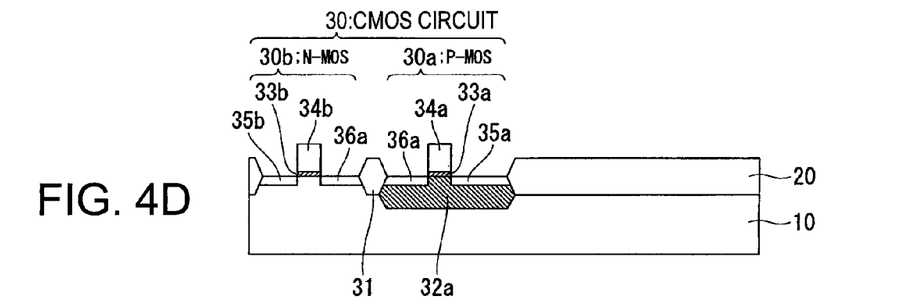

Next, as shown in FIG. 4C, the gate insulation film 33 and the poly-Si layer 34 are removed from a region excluding the gate electrodes of the P-MOS transistor 30a and the N-MOS transistor 30b by being patterned with a photolithography method so as to form the gate insulation film 33a and the gate electrode 34a of the P-MOS transistor 30a and the gate insulation film 33b and the gate electrode 34b of the N-MOS transistor 30b. Then, as shown in FIG. 4D, P-type impurity ions are doped into the N-type well 32a by using an ion implantation method so as to form the source region 35a and the drain region 36a of the P-MOS transistor 30a. Likewise, by using an ion implantation method, N-type impurity ions are doped into the semiconductor substrate 10 so as to form the source region 35b and the drain region 36b of the N-MOS transistor 30b. After being doped, the impurity ions are heat treated so as to be activated.

Through the above steps, the CMOS circuit 30 (P-MOS transistor 30a and the N-MOS transistor 30b) is formed in the CMOS circuit forming region on the semiconductor substrate 10.

Figure 5A:
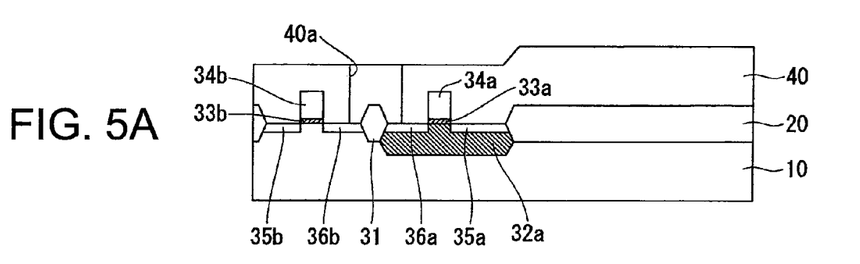
FIGS. 5A to 5C are explanatory views of the method for manufacturing the semiconductor sensor of the embodiment.

Subsequently, insulation sidewalls for gate electrodes 34a and 34b are formed if required. Then, as shown in FIG. 5A (sidewalls are not shown), the first interlayer film 40 is formed on the semiconductor substrate 10 (including the CMOS circuit 30) and the LOCOS film 20. In the embodiment, the first interlayer film 40 is formed as follows. $SiO_2$ film is formed with a thickness of about 1000 angstrom by using a CVD method as a low temperature oxide (LTO) film or a high temperature oxide (HTO) film. Then, a TEOS film is deposited on the $SiO_2$ film with a thickness of about 8000 angstrom by using a CVD method. Examples of the insulation film used for the first interlayer film 40 may include a phosphor silicate glass (PSG) film, a boron phosphor silicate glass (BPSG) film, and combinations of them in addition to the silicon dioxide ($SiO_2$) film and the tetra-ethoxy-silane (TEOS) film described above. After the first interlayer film 40 is formed, the contact hole 40a is formed by etching so as to couple the CMOS circuit 30 to the surface acoustic wave element 120. In this step, it is necessary that part of the drain region 36a of the P-MOS transistor 30a and part of the drain region 36b of the N-MOS transistor 30b are included in the opening region of the contact hole 40a.

Figure 5B:
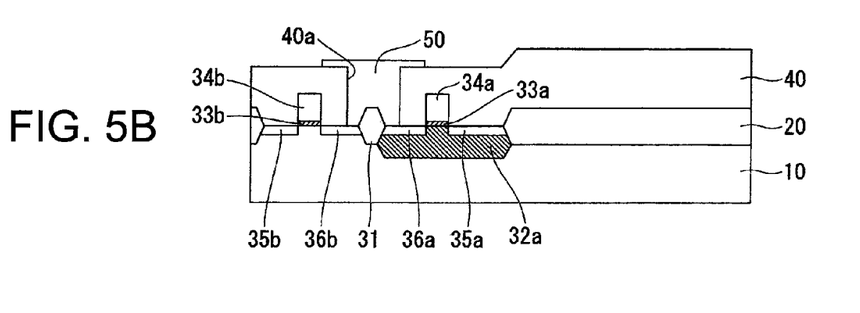
Figure 5C:
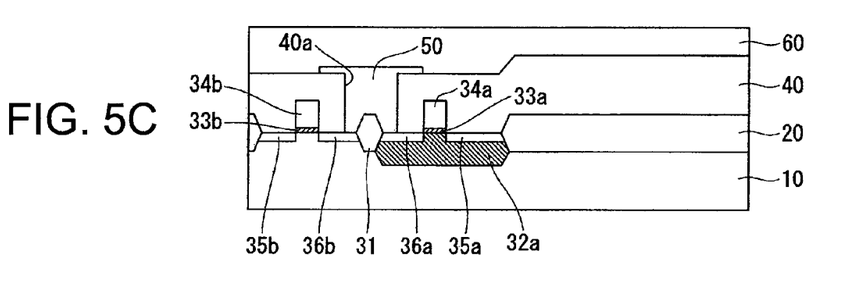

Then, as shown in FIG. 5B, a metal layer (e.g., Al—Cu) deposited on the contact hole 40a and the first interlayer film 40 by a sputtering method are patterned by a photolithography method and etched so as to form the CMOS output electrode 50. As a result, the drain region 36a of the P-MOS transistor 30a and the drain region 36b of the N-MOS transistor 30b in the CMOS circuit 30 are electrically coupled. Next, as shown in FIG. 5C, a TEOS film is exemplarily formed on the first interlayer film 40 and the CMOS output electrode 50 as the second interlayer film 60 by using a CVD method, and then the surface of the second interlayer film 60 is planarized by using a chemical mechanical polishing (CMP) method. When a second metal wiring layer (e.g., gate wiring lines connected to the gate electrodes 34a and 34b, and source wiring lines connected to the source regions 35a and 35b) is required in the CMOS circuit 30, a third interlayer film (not shown) is formed and planarized.

Figure 6A:
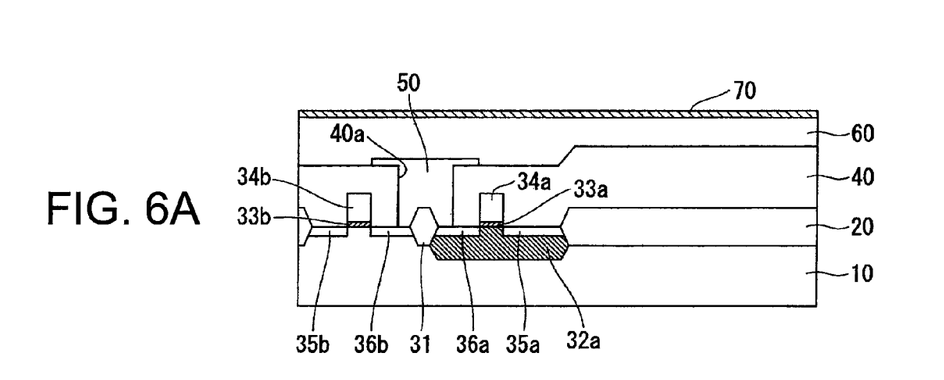
FIGS. 6A to 6C are explanatory views of the method for manufacturing the semiconductor sensor of the embodiment.
Figure 6B:
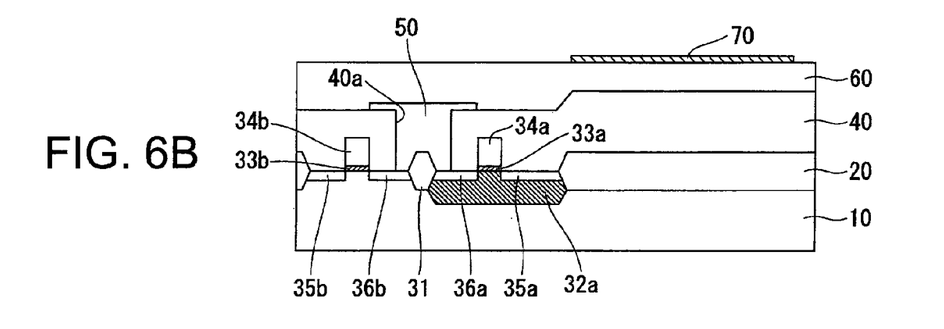

Next, as shown in FIG. 6A, the metal thin film (Pt) 70 is deposited on the second interlayer film 60 by using a CVD method. Then, as shown in FIG. 6B, the metal thin film 70 is left only in the surface acoustic wave element forming region on the second interlayer film 60 by being patterned by using a photolithography method and etched. As described above, the metal thin film 70 is made of a metal having a function to facilitate the crystal growth of the wurtzite structure of the first piezoelectric thin film 80, which is formed in the subsequent step, in the c-axis direction. Thus, the crystal property of the metal thin film 70 significantly influences the crystal property of the first piezoelectric thin film 80. From this point of view, the metal thin film 70 preferably has a thicker thickness. In the embodiment, the full-width at half-maximum of the X-ray diffraction pattern, which is an index of the crystal property, can be 2 degrees or less when the thickness of the metal thin film 70 made of Pt is 1000 angstrom or more. As metal for the metal thin film 70, one of the following metals having a lower value of the full-width at half-maximum may be used in addition to Pt. The metals are Au, Al, Ag, Cu, Mo, Cr, Nb, W, Ni, Fe, Ti, Co, Zn, and Zr.

In order to improve adhesiveness between the metal thin film 70 and the second interlayer film 60 under the film 70, a Ti film may be formed with a thickness of about 100 angstrom to about 1000 angstrom therebetween. Examples of such material for a thin film improving the adhesiveness may include silicide metals of Co, Ni, W, and Mo, in addition to Ti.

Figure 6C:
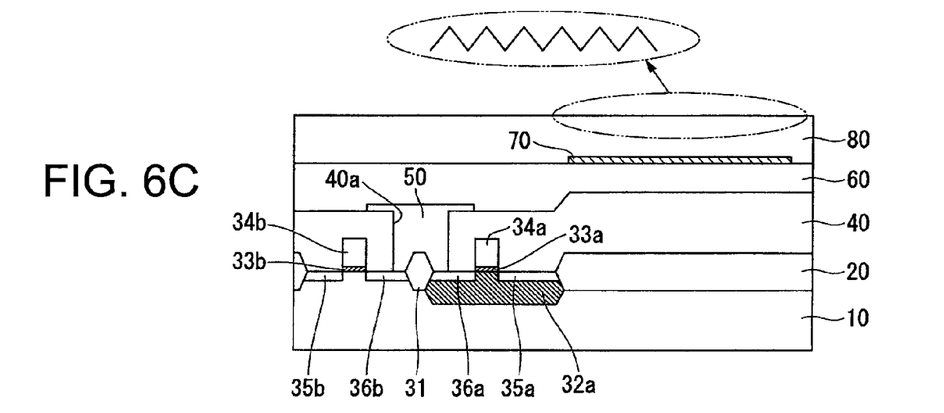

Then, as shown in FIG. 6C, the first piezoelectric thin film 80 (AlN) is formed on the second interlayer film 60 and metal thin film 70 with a thickness of from about 8000 angstrom to about 15000 angstrom. In the embodiment, the first piezoelectric thin film 80 was formed by using a reactive sputtering method in which a pure Al target is sputtered in an atmosphere containing Ar and $N_2$. In order to grow the crystal grain of the AlN film to a larger size, the conditions were set and regulated within the following ranges: the film forming pressure was from 0.05 Pa to 2.0 Pa; the substrate temperature was from 150 degrees centigrade to 400 degrees centigrade; and the flow rate ratio of Ar/$N_2$ was from 0.0 to 1.0. As the result, it was confirmed that the first piezoelectric thin film 80 on the metal thin film 70 was grown to a columnar crystal oriented and aligned in the c-axis direction of the wurtzite structure with a grain size of 80 nm to 200 nm. In addition, a ridge-and-valley portion corresponding to the grown crystal grain size formed on the uppermost surface of the first piezoelectric thin film 80 was confirmed. The surface roughness of the first piezoelectric thin film 80 was about 10 nm to about 50 nm according to the observation on the surface by an atomic force microscope (AFM).

Figure 7A:
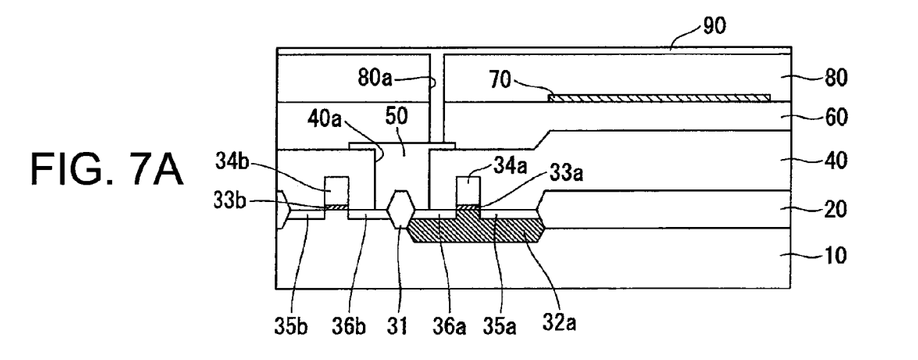
FIGS. 7A to 7C are explanatory views of the method for manufacturing the semiconductor sensor of the embodiment.
Figure 7B:
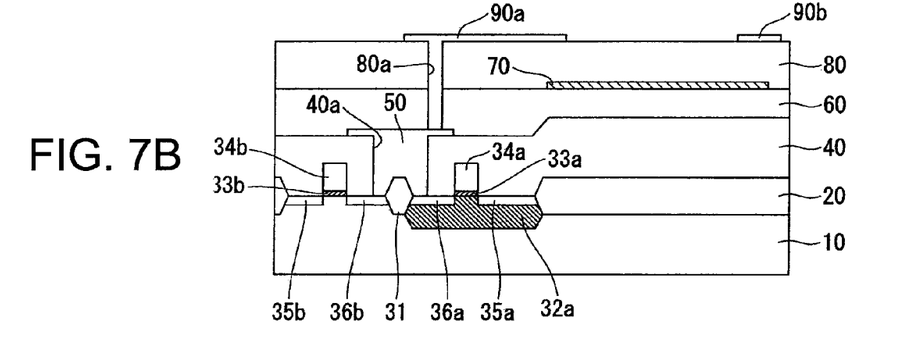

Next, as shown in FIG. 7A, the first piezoelectric thin film 80 and the second interlayer film 60 are etched by using a photolithography method so as to form the via hole 80a to couple the CMOS circuit 30 to the surface acoustic wave element 120, and then the Al electrode film 90 is formed with a thickness of about 1000 angstrom by using a sputtering method. The first piezoelectric thin film 80 (AlN film) is etched with a strong alkaline solution such as tetramethyl ammonium hydroxide (TMAH) while the second interlayer film 60 (TEOS film) is dry-etched. The Al electrode film 90 is formed by using the reactive sputtering method in which the $N_2$ gas supply is stopped after being used for forming the first piezoelectric thin film 80 so as to form a pure Al electrode film. Then, as shown in FIG. 7B, the Al electrode film 90 is patterned by using a photolithography method and etched so as to form the interdigital electrode (the first electrode 90a and the second electrode 90b) for the surface acoustic wave element 120.

Figure 7C:
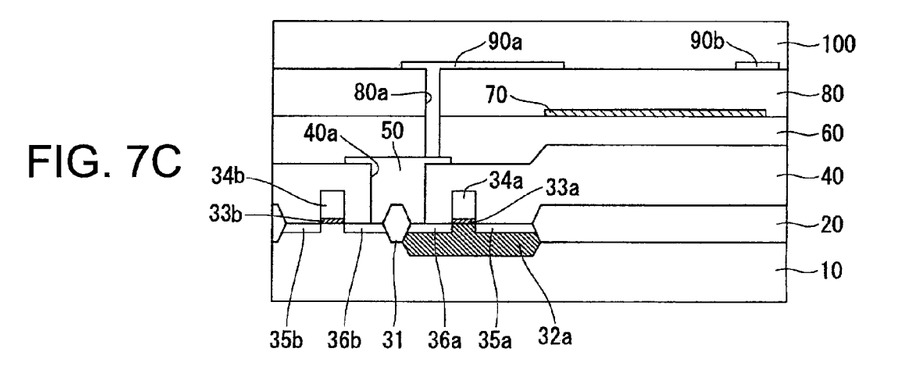

Next, as shown in FIG. 7C, the second piezoelectric thin film 100 (AlN film) is formed on the first electrode 90a, the second electrode 90b, and the first piezoelectric thin film 80 with a thickness of about 8000 angstrom to about 15000 angstrom by using a reactive sputtering method used for forming the first piezoelectric thin film 80. Since the second piezoelectric thin film 100 grows following the surface morphology of the first piezoelectric thin film 80, the second piezoelectric thin film 100 grows to have a crystal grain size larger than that of the first piezoelectric thin film 80 (grown to about 500 nm). Accordingly, the ridge-and-valley portion formed on the uppermost surface of the second piezoelectric thin film 100 is larger than that of the first piezoelectric thin film 80.

Figure 8A:
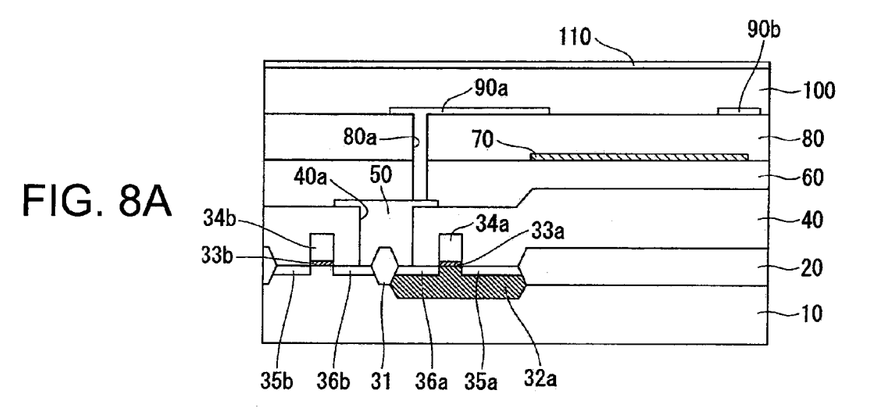
FIGS. 8A and 8B are explanatory views of the method for manufacturing the semiconductor sensor of the embodiment.
Figure 8B:
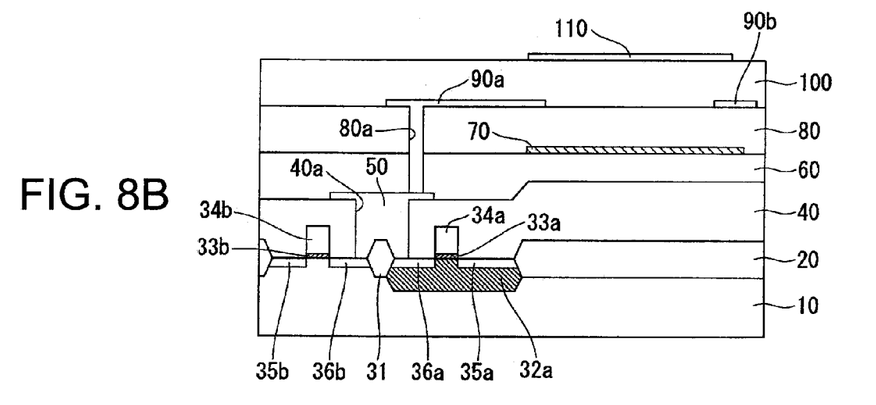

Subsequently, as shown in FIG. 8A, the sensitive film 110 on which molecules adsorb is deposited on the second piezoelectric thin film 100 by using a CVD method or a sputtering method. Next, as shown in FIG. 8B, the sensitive film 110 is patterned by a photolithography method, and then the sensitive film 110 is etched so that at least the film 100 formed on the ridge-and-valley portion on the surface of the second piezoelectric thin film 100 is left. As a result, the sensitive film 110 of the surface acoustic wave element 120 is formed.

Through the method described as above, the semiconductor sensor SS of the first embodiment can be manufactured. In addition, according to the method of the second embodiment, the metal thin film 70 can be formed by using conventional semiconductor manufacturing processes without employing a particular process for enlarging the surface area of the sensitive film 110 as necessary in related art, e.g., JP-A-2007-147556. Thus, the manufacturing costs can be reduced.

The invention is not limited to the embodiments, the following modifications can be exemplified.

Figure 9A:
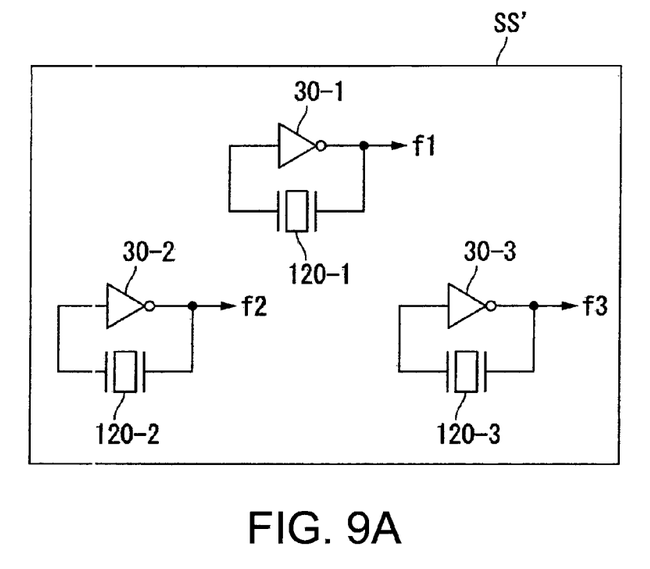
FIGS. 9A and 9B are explanatory views illustrating modifications of the semiconductor sensor of the embodiment.

In the embodiments, the semiconductor sensor SS is exemplarily described that is provided with a single oscillation circuit including the CMOS circuit 30, the surface acoustic wave element 120, the feedback resistor 200, the input side capacitor 210, and the output side capacitor 220. However, a plurality of oscillation circuits may be included. For example, in FIG. 9A, a semiconductor sensor SS' is shown that is provided with 3 oscillation circuits. A first oscillation circuit (only a CMOS circuit 30-1 and a surface acoustic wave element 120-1 are shown to be simplified for convenience) generates an oscillation frequency f1. A second oscillation circuit (only a CMOS circuit 30-2 and a surface acoustic wave element 120-2 are shown to be simplified for convenience) generates an oscillation frequency f2. A third oscillation circuit (only a CMOS circuit 30-3 and a surface acoustic wave element 120-3 are shown to be simplified for convenience) generates an oscillation frequency f3. Measuring and averaging the changes of oscillation frequencies f1, f2, and f3 of the oscillation circuits allow more accurately detecting chemical substances.

Figure 9B:
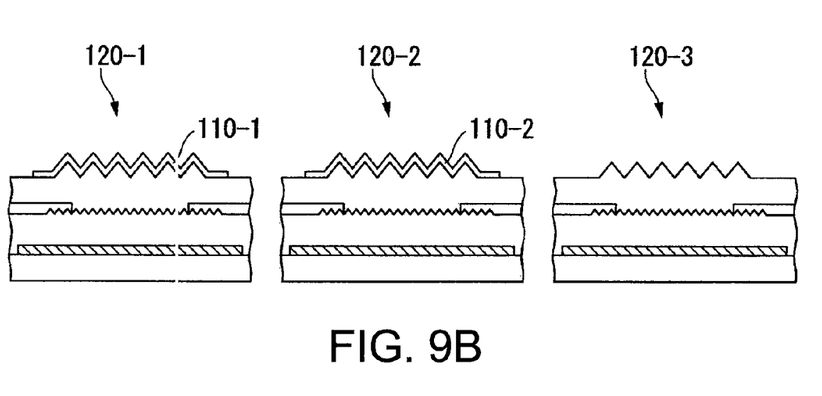

For another modification, as shown in FIG. 9B, the surface acoustic wave element 120-3 that does not have the sensitive film 110 is provided as a reference element so as to use the oscillation frequency f3 as a reference frequency. Comparing the oscillation frequencies f1 and f2 of the other oscillation circuits with the reference frequency allows more easily detecting the frequency varied by adsorption of gas molecules. As a result, a semiconductor sensor having a higher sensitivity can be provided.

In the embodiments, the CMOS inverter is exemplarily described as an inverter circuit used for the oscillation circuit. However, semiconductor elements other than CMOS may be used to structure the inverter circuit. In the embodiments, the surface acoustic wave element 120 including two piezoelectric thin film layers is exemplarily described, but more than two piezoelectric thin film layers may be included if required.

What is claimed is:

1. A semiconductor sensor, comprising:
   a semiconductor substrate;
   a plurality of piezoelectric thin films layered on the semiconductor substrate, the plurality of piezoelectric thin films including at least a pair of the piezoelectric thin films layered above and below;
   a pair of electrodes that are formed at an interface of at least the pair of the piezoelectric thin films layered above and below and excite surface acoustic waves;
   a thin film directly under a lowest-layer piezoelectric film of the piezoelectric thin films;
   a metal thin film that is formed at an interface of the lowest-layer piezoelectric thin film and the thin film, and facilitate a growth of a ridge-and-valley portion on a surface of an uppermost-layer piezoelectric thin film of the piezoelectric thin films; and
   a sensitive film for molecular adsorption formed on at least the ridge-and-valley portion on the uppermost-layer piezoelectric thin film.

2. The semiconductor sensor according to claim 1, wherein the metal thin film is a metal facilitating a crystal growth of a wurtzite structure of the piezoelectric thin films in a c-axis direction.

3. The semiconductor sensor according to claim 2, wherein the metal thin film is any one of Pt, Au, Al, Ag, Cu, Mo, Cr, Nb, W, Ni, Fe, Ti, Co, Zn, and Zr.

4. The semiconductor sensor according to claim 1 further comprising:
   an oscillation circuit, the circuit including:
      an inverter circuit layered between the lowest-layer piezoelectric thin film and the semiconductor substrate; and
      a surface acoustic wave element having the metal thin film, the pair of the piezoelectric thin films, the pair of the electrodes, and the sensitive film, wherein the inverter circuit and the acoustic wave element are electrically coupled.

5. The semiconductor sensor according to claim 4, wherein the inverter circuit includes a CMOS circuit.

6. The semiconductor sensor according to claim 4, wherein the oscillation circuit includes a plurality of the oscillation circuits, and the surface acoustic wave element included in at least one of the plurality of oscillation circuits is used as a reference element having no sensitive film.

7. A method for manufacturing a semiconductor sensor, comprising:
   (a) layering a plurality of piezoelectric thin films on a semiconductor substrate, the plurality of piezoelectric thin films including at least a pair of the piezoelectric thin films layered above and below;
   (b) forming a pair of electrodes at an interface of the pair of the piezoelectric thin films, the electrodes exciting surface acoustic waves;
   (c) forming a metal thin film at an interface of a lowest-layer piezoelectric thin film of the piezoelectric thin films and a thin film directly under the lowest-layer piezoelectric film, the metal thin film facilitating a growth of a ridge-and-valley portion on a surface of an uppermost-layer piezoelectric thin film of the piezoelectric thin films; and
   (d) forming a sensitive film for molecular adsorption at least on the ridge-and-valley portion on the uppermost-layer piezoelectric thin film.

8. The method for manufacturing a semiconductor sensor according to claim 7, wherein in step (c), the metal thin film is a metal facilitating a crystal growth of a wurtzite structure of the piezoelectric thin films in a c-axis direction.

9. The method for manufacturing a semiconductor sensor according to claim 8, wherein the metal thin film is any one of Pt, Au, Al, Ag, Cu, Mo, Cr, Nb, W, Ni, Fe, Ti, Co, Zn, and Zr.

10. The method for manufacturing a semiconductor sensor according to claim 9, wherein, in step (c), the metal thin film is formed by using Pt with a thickness of 1000 angstrom or more.

11. The method for manufacturing a semiconductor sensor according to claim 7, wherein, in step (a), the lowest-layer piezoelectric thin film is formed with AlN by using a reactive sputtering method by sputtering a pure Al target in an atmosphere containing Ar and $N_2$ with a thickness of 8000 angstrom to 15000 angstrom under a film forming condition in which film forming pressure is within a range from 0.05 Pa to 2.0 Pa, a semiconductor substrate temperature is within a range of 150 degree centigrade to 400 degrees centigrade, and a flow rate ratio of Ar to $N_2$ is within a range of 0.0 to 1.0.

12. The method for manufacturing a semiconductor sensor according to claim 7, further comprising:
   (e) forming an inverter circuit between the lowest-layer piezoelectric thin film and the semiconductor substrate; and
   (f) forming a wiring line electrically coupling a surface acoustic wave element including the metal thin film, the pair of the piezoelectric thin films, the pair of the electrodes, and the sensitive film, and the inverter circuit so as to structure an oscillation circuit.

13. The method for manufacturing a semiconductor sensor according to claim 12, wherein, in step (e), the inverter circuit includes a CMOS circuit.

14. The method for manufacturing a semiconductor sensor according to claim 12, wherein the oscillation circuit includes a plurality of the oscillation circuits, and in step (d), the sensitive film is not formed in the surface acoustic wave element included in at least one of the plurality of oscillation circuits.

* * * * *